(12) United States Patent
Yu et al.

(10) Patent No.: US 6,713,513 B2
(45) Date of Patent: Mar. 30, 2004

(54) METHOD FOR TREATING CARTILAGE RELATED DISEASES

(75) Inventors: Kai Yu, Beijing (CN); Zhiwen Wang, Beijing (CN); Xiangguo Dai, Beijing (CN)

(73) Assignee: Juneng Industry Co., Ltd., Beijing (CN)

( * ) Notice: Subject to any disclaimer, the term of this patent is extended or adjusted under 35 U.S.C. 154(b) by 21 days.

(21) Appl. No.: 10/039,764

(22) Filed: Dec. 31, 2001

(65) Prior Publication Data

US 2003/0050342 A1 Mar. 13, 2003

(30) Foreign Application Priority Data

Jul. 3, 2001 (CN) .......................... 01 1 15784

(51) Int. Cl.$^7$ .................. A61K 31/198; A61K 31/19; A01N 33/02
(52) U.S. Cl. .................. 514/561; 514/663; 514/671; 514/557; 514/502; 514/561
(58) Field of Search ................ 514/663, 671, 514/561, 557, 502

(56) References Cited

U.S. PATENT DOCUMENTS

| | | | | |
|---|---|---|---|---|
| 6,077,872 A | * | 6/2000 | Yu et al. ........... | 514/663 |
| 6,313,170 B1 | * | 11/2001 | Yu et al. ........... | 514/557 |
| 6,468,980 B1 | * | 10/2002 | Jariwalla ........... | 514/34 |
| 6,548,687 B1 | * | 4/2003 | Yu et al. ........... | 556/61 |

FOREIGN PATENT DOCUMENTS

| | | | | |
|---|---|---|---|---|
| CN | 1143464 A | * | 2/1997 | |
| CN | 1215592 A | * | 5/1999 | |
| CN | 1305751 A | * | 8/2001 | |
| WO | WO 99/11256 A1 | * | 3/1999 | |
| WO | WO 00/10962 A1 | * | 3/2000 | |

OTHER PUBLICATIONS

Review Article by Neil Gonter, Department of Rheumatology, University of Pennsylvania Healthsystem, 2002.*
"Lean about Arthritis", WholeHealthMD.com, 2000.*

* cited by examiner

Primary Examiner—Zohreh Fay
Assistant Examiner—Brian S. Kwon
(74) Attorney, Agent, or Firm—Alston & Bird LLP

(57) ABSTRACT

The present invention relates to a method for preventing or treating of cartilage related diseases, such as osteoarthritis, rheumatoid arthritis, articular cartilage damage, multiple chondritis, osteochondrosis, etc., which comprises administering an effective amount of calcium L-threonate to a subject in need of such prevention or treatment. It had been demonstrated by experiments that calcium L-threonate could improve significantly the positive expression percentage of collagen I mRNA in the chondrocyte and osteoblast, improved significantly the positive expression percentage of articular cartilage and epiphyseal cartilage, facilitated the growth of chondrocyte, increased the quantity of bone collagen, and promoted the formation of bone and cartilage matrix and the synthesis of proteoglycan. It could also promote the formation of bone nourishing blood vessels and improve the microcirculation of bone.

9 Claims, 10 Drawing Sheets

METHOD FOR TREATING CARTILAGE RELATED DISEASES

BACKGROUND OF THE INVENTION

The invention relates to a method for preventing or treating cartilage related diseases, and particularly a method for preventing or treating cartilage related diseases by administering an effective amount of calcium L-threonate to a subject suffering from such diseases.

There are many kinds of cartilage related diseases, the common examples of which are osteoarthritis, rheumatoid arthritis, multiple chondritis, articular cartilage damage, and osteochondrosis, etc. These diseases are often accompanied by the loss of cartilage.

Osteoarthritis is also called retrograde arthropathy, hyperplastic osteoarthritis. Its main characteristic is the formation of new bone accompanied with cartilage retrograde affection. Based on preliminary epidemiological investigations, the morbidity rate of osteoarthritis of knee joints in China is 9.56%. The rate reaches 78.5% among the people more than 60 years old, which is similar to that of western countries. Regretfully, there are no effective drugs available to treat osteoarthritis. The non-steroidal drugs are mainly used, such as Ibuprofen, Naproxen, etc. They have certain effects of alleviating pain, however, they have severe side effects and can not cure the disease in essence.

The occurrence of osteoarthritis is related to obesity, bone density, trauma and force burden, and heredity (see, Internal Medicine, 4th ed., Chen Haozhu, Li Zongming, etc.). Articular cartilage is formed by the aggregation of collagen fibers with a thickness of 1–2 mm, glucoprotein and hyaluronate. It functions by hydration as a cushion to absorb and disperse the endured burden and mechanical force. Under physiological conditions, articular cartilage depends on the contraction of muscles around the joint and the subchondral bone to fulfil the above-mentioned task. When there is something wrong with the muscles around the joint and the subchondral bone, for example, the subchondral bone has an abnormality such as senile retrograde change, osteoporosis, or the muscles endure excessive pressure such as obesity, trauma, etc., this can lead to the damage of cartilage, and possibly lead to osteoarthritis. What is worth mentioning herein is bone density. When the subchondral bone trabeculae become thin and stiff, their tolerance to endure pressure will decrease, and therefore the probability of the occurrence of osteoarthritis in the patient suffered from osteoporosis increases.

The pathologic changes of osteoarthritis show that articular cartilage degenerates firstly, then the loss of glucoprotein in the cartilage matrix softens the cartilage in the superficial layer of the joint. Fracture occurs in the part which endures pressure, causing the surface of the cartilage to have the appearance of velvet. Then the cartilage exfoliates gradually and the cartilage layer becomes thin or even disappears. Microfracture and sclerosis occur in the subchondral bone. Hyperosteogeny in the articular surface and its surrounding bone form the osteopetrosis, osteophyte and bone cystic degeneration in the X-line (epiphyseal line).

Rheumatoid arthritis and multiple chondritis are related to autoimmunity. Their common characteristics are the damage and loss of cartilage.

Damage of articular cartilage is acute or chronic damage of articular cartilage, which often appears in sport injuries. An example of acute damage is simple cartilage fracture. Chronic damage appears as retrograde affection and degeneration of cartilage, which will develop to osteoarthritis in the long term.

Osteochondrosis is an idiopathic disease of epiphysis in children, the characteristics of which are ischemic necrosis of epiphysis and disturbance of endochondral ossification in epiphysis, which finally can lead to malformed joints. It can be seen from the above that cartilage related diseases are often related to the damage, loss and functional degradation of cartilage.

The inventors conducted research on this, and found that calcium L-threonate could significantly improve the positive expression percentage of mRNA of collagen I in chondrocytes and osteoblasts, could significantly increase the positive expression percentage of chondrocytes in articular cartilage and epiphyseal cartilage, promote the growth of chondrocytes, increase the quantity of bone collagen, and promote the growth of bone, formation of cartilage matrix and the synthesis of protein mucopolysaccharide. It can also promote the formation of nourishing blood vessels in the bone and improve the microcirculation of the bone.

Therefore, it is an object of the present invention to provide a method for preventing or treating of cartilage related diseases, in particular a method for preventing or treating of cartilage related diseases, such as osteoarthritis, rheumatoid arthritis, multiple chondritis, articular cartilage damage and osteochondrosis, etc.

It is another object of the present invention to provide a pharmaceutical composition for preventing or treating cartilage related diseases, comprising an effective amount of the calcium L-threonate of the present invention and a pharmaceutically acceptable carrier.

It is a further object of the present invention to provide a calcium L-threonate compound for preventing or treating cartilage related diseases.

It is also an object of the present invention to provide a new use of calcium L-threonate in the preparation of a pharmaceutical composition for preventing or treating cartilage related diseases.

It is also an object of the present invention to provide a new use of calcium L-threonate to prevent or treat cartilage related diseases.

BRIEF SUMMARY OF THE INVENTION

The present invention provides a method for preventing or treating cartilage related diseases, in particular a method for preventing or treating cartilage related diseases, such as osteoarthritis, rheumatoid arthritis, multiple chondritis, articular cartilage damage, osteochondrosis, diseases related to cervical vertebra or diseases related to lumbar vertebra, etc., which comprises administering an effective amount of calcium L-threonate to a subject suffering from said diseases.

The present invention also provides a pharmaceutical composition for preventing or treating cartilage related diseases, comprising an effective amount of the calcium L-threonate of the present invention and pharmaceutically acceptable carrier.

The present invention also provides a calcium L-threonate compound for preventing or treating cartilage related diseases.

The present invention further provides a new use of calcium L-threonate in the manufacture of a pharmaceutical composition for preventing or treating cartilage related diseases.

The present invention further provides a new use of calcium L-threonate to prevent or treat cartilage related diseases.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

Figure 1:
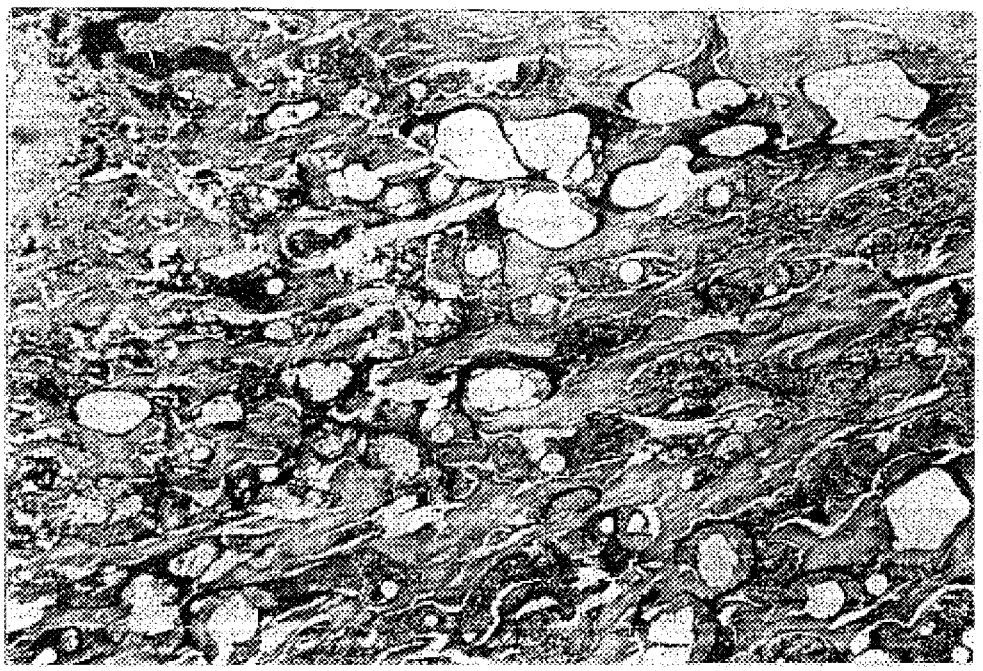
FIG. 1 is a diagram of MS histochemical staining of cancellous bone of metaphysis in blank-control group, showing mature osteocollagenous fibers.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The calcium L-threonate of the present invention is white powder, scarcely with odor. It is soluble in water but insoluble in alcohol, ether and chloroform and has a formula $C_8H_{14}O_{10}Ca$ and a chemical structural formula represented by:

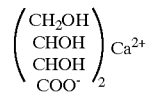

The compound can be prepared by: a certain amount of L-ascorbic acid (Vc) was added to water and dissolved, then calcium carbonate was slowly added into the mixture with stirring. To the above mixture, hydrogen peroxide was added dropwise at a temperature between 10° C. and 60° C. and the temperature was maintained for 1–4 hours at 40–80° C. After active charcoal was added, the mixture was filtered. The filtrate was concentrated at a temperature between 30° C. and 90° C. and crystallized at ambient temperature. The crystal was dried at a temperature of 50–100° C.

In the above process of preparing calcium L-threonate, the addition of calcium carbonate must be carried out very slowly to avoid loss of material out of the container due to production of carbon dioxide gas.

The above process of preparing calcium L-threonate may further comprise the operation of washing the cake obtained by filtering the mixture that had been treated with active charcoal, twice with hot water of 80° C. and the operation of concentrating the combined washes and filtrate.

The above process of preparing calcium L-threonate is advantageous for its reasonable procedure, simple operation, good yield as high as 90% and high purity of product. The preparation method of calcium L-threonate is described in U.S. Pat. No. 6,077,872, issued on Jun. 20, 2000 to Kai Yu et al., which is incorporated herein by reference.

Of course, the calcium L-threonate of the present invention may also be prepared by the other methods known in the prior art.

The calcium L-threonate of the present invention may be administered orally. The calcium L-threonate of the present invention may be used in various forms of formulations, such as tablets, capsules and other forms of pharmaceutically acceptable compositions.

The pharmaceutical composition according to the present invention contains a certain amount of calcium L-threonate as an active ingredient, along with a pharmaceutically acceptable carrier, which can be various carriers that have been widely used in medicaments in the prior art such as excipients. The pharmaceutical composition of the present invention can be prepared by the methods known in the art, such as mixing, pelleting and tabletting.

The pharmaceutical composition of the present invention may also contain other optional ingredients that can be used in pharmacology, such as perfumes, colorants and sweetening agents, etc. The preferred pharmaceutical composition of the present invention contains 60%, preferably 80%, more preferably 90% by weight of calcium L-threonate with other excipients and optional components as make-ups.

The dosage of calcium L-threonate may vary depending on the age of patients. As guidance, the dosage of calcium L-threonate for an adult is typically between 0.5 g and 12 g per day, preferably between 3 g and 7 g per day. For children, the dosage may be decreased according to their weights.

The experiments of pharmacokinetics of calcium L-threonate in animal bodies demonstrated that the absorption metabolism of calcium L-threonate in rat satisfied the One-Chamber model. The absorption of calcium L-threonate was relatively slower but more complete, the peak of serum calcium concentration arrived later ($T_{max}$=0.79 hrs), and its half-life was longer ($T_{1/2}$=4.45 hrs) than those of other calcium agents such as calcium gluconate, calcium acetate, and calcium carbonate. Calcium L-threonate can stay in serum for a longer time at a higher level. The area under the curve (AUC) equals to 191.75 g/(ml.hr). The pharmacokinetic test of calcium L-threonate is described in U.S. Pat. No. 6,077,872, issued on Jun. 20, 2000 to Kai Yu et al., which is incorporated herein by reference.

In the present invention, we have studied the influence of calcium L-threonate on the mRNA expression of chondrocytes and osteoblasts, and the positive expression percentage of chondrocytes. The details of this study are described in the experiment hereinafter.

Experiment: Influence of calcium L-threonate on the mRNA expression of chondrocytes and osteoblasts, and the positive expression percentage of chondrocytes.

The research methods and the results were as follows:

I. Objects of the Experiment

To study whether calcium L-threonate had the effects of promoting the mRNA expression of collagen I on the bone tissue of the rat with osteoporosis caused by retinoic acid and whether the formation of collagen I had the effects of improving the formation of cartilage and bone.

II. Experimental Method

1. Grouping of animals: 66 male 3-month-aged rats were used in the present test. Eight rats were randomly selected as blank-control group, which were fed with normal diet and tap water. The other 58 rats were randomly divided into 9 groups, and were continuously administered retinoic acid with a dosage of 70 mg/kg body weight and volume of 10 ml/kg body weight, and were fed with low calcium diet meanwhile. After two weeks of administration of retinoic acid, stop the drug and thus establishing osteoporosis models.

(1) Blank-control group: 8 rats, fed normal diet and tap water
(2) Model-control group: 6 rats, fed physiological saline
(3) Caltrate-D group: 6 rats, administered caltrate-D with a dosage of 300 mg/kg body weight (containing vitamin D 62.5 IU/kg body weight)
(4) Calcium citrate group: 6 rats, administered calcium citrate with a dosage of 100 mg/kg body weight
(5) Sodium hydroxyethyl phosphate group: 6 rats, administered sodium hydroxyethyl phosphate with a dosage of 100 mg/kg body weight
(6) Calcium L-threonate group I: 6 rats, administered calcium L-threonate with a dosage of 50 mg/kg body weight
(7) Calcium L-threonate group II: 7 rats, administered calcium L-threonate with a dosage of 100 mg/kg body weight
(8) Calcium L-threonate group III: 9 rats, administered calcium L-threonate with a dosage of 200 mg/kg body weight.

The rats were administered drugs for 10 weeks, respectively. During the whole test period, each group was fed with low calcium diet and de-ionized water except that the blank-control group was fed with normal diet. Then the lower one third of right femur of each rat was extracted, and preserved at −20° C.

2. Reagents and Method (1) Hybridization in situ and immunohistochemical assay:

Collagen I was stained by hybridization in situ, following the directions of the kit. After specific hybridization, mRNA of collagen I was developed by 3,3'-diaminobenzidine (DAB). The slide was routinely dehydrated and mounted. (The detection kit was provided by Wuhan Doctor Microbiologic Engineering Co. Ltd., China. Cat. No: MK1171.)

Collagen I was immunohistochemically stained by ABC method, following the directions of kit. Collagen I was developed by DAB. The slide was routinely dehydrated and mounted. (The detection kit was provided by Wuhan Doctor Microbiologic Engineering Co. Ltd., China. Cat. No: BA0325)

(2) Histochemical Staining a Masson-Goldner Lrichrone staining (M-S staining)
b Toluidine Blue staining (T-B staining)
c Hematoxylin-eosin (HE) staining
d Von Kossa silver staining of partial slice (V-K silver staining).

III. Statistical Processing

The results were observed by microscopy, which was expressed by positive percentage. X2 test was conducted to the experimental data.

Figure 2:
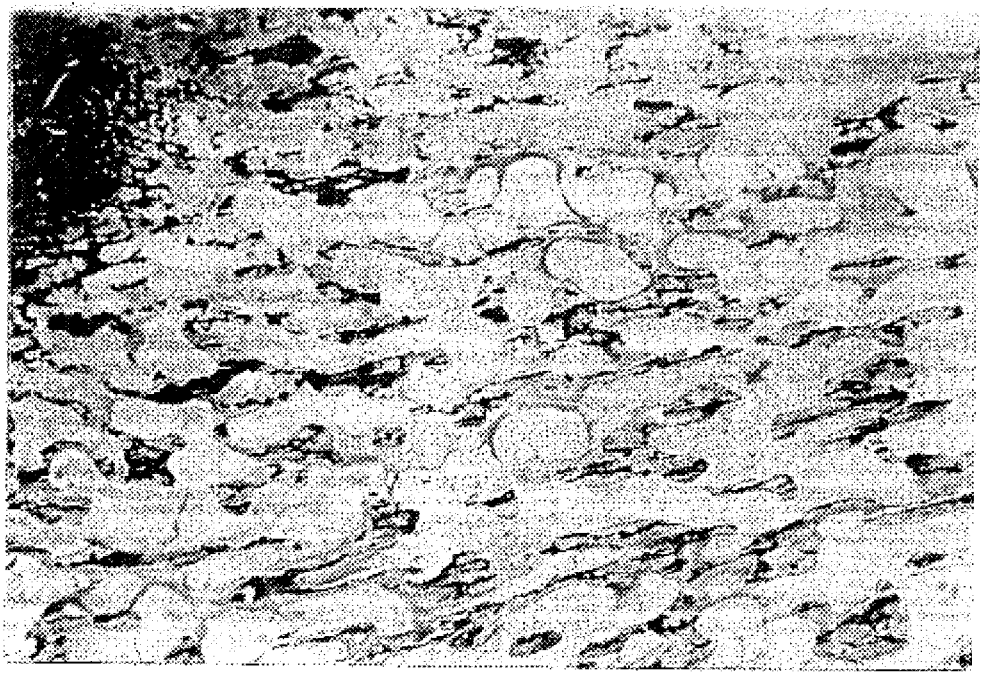
FIG. 2 is a diagram of staining of glycogen in the cancellous bone of metaphysis in blank-control group, showing even distribution of glycogen.
Figure 3:
FIG. 3 is a diagram of MS histochemical staining of cancellous bone in model group, showing sparse bone trabecula accompanied by microfracture.
Figure 4:
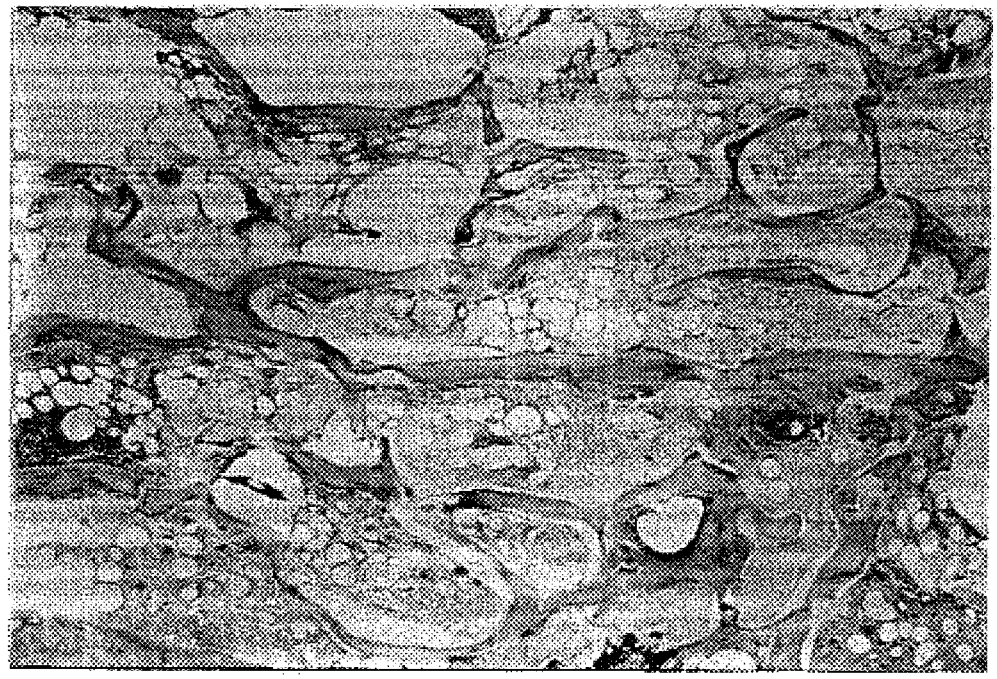
FIG. 4 is a diagram of histochemical staining of glycogen in the cancellous bone in model group, showing sparse bone trabeculae and decreased synthesis of glycogen, accompanied by microfracture.
Figure 12:
FIG. 12 is a diagram of histochemical MS staining in sodium hydroxyethyl phosphate group, showing mature cancellous bone and sparse oesteocollagenous fibers.
Figure 14:
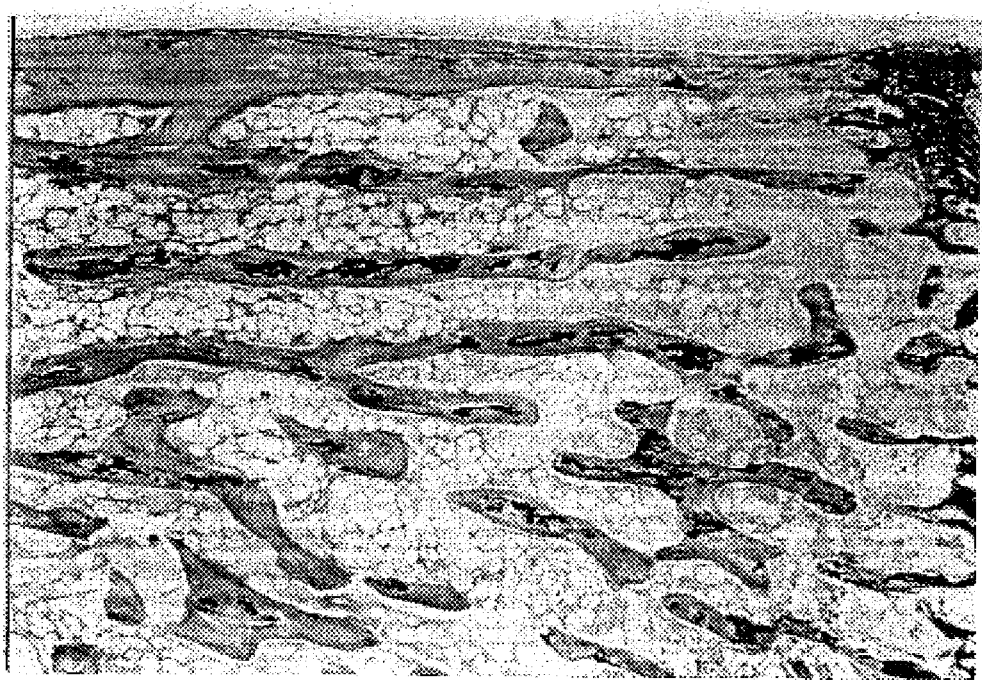
FIG. 14 is a diagram of staining of glycogen in calcium L-threonate group, showing thick, dense and ordered bone trabeculae in cancellous bone and abundant glycogen (++).
Figure 17:
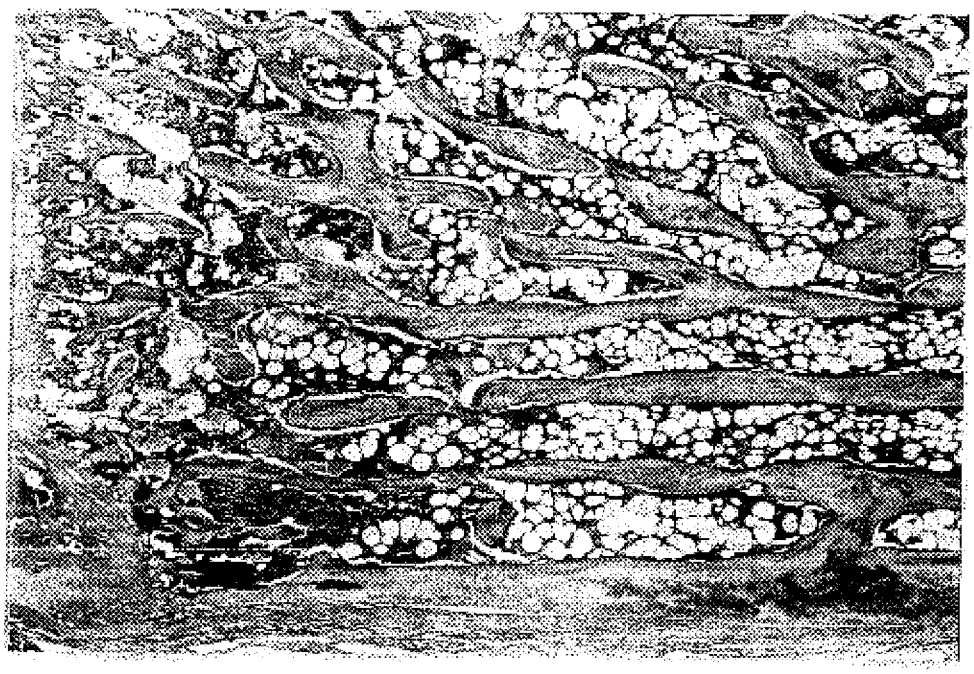
FIG. 17 is a diagram of histochemical MS staining in calcium L-threonate group, showing ordered bone trabeculae with increased density in cancellous bone and increased synthesis of collagen.
Figure 18:
FIG. 18 is a diagram of silver staining in calcium L-threonate group, showing abundant newborn osteocytes with clear borders.
Figure 19:
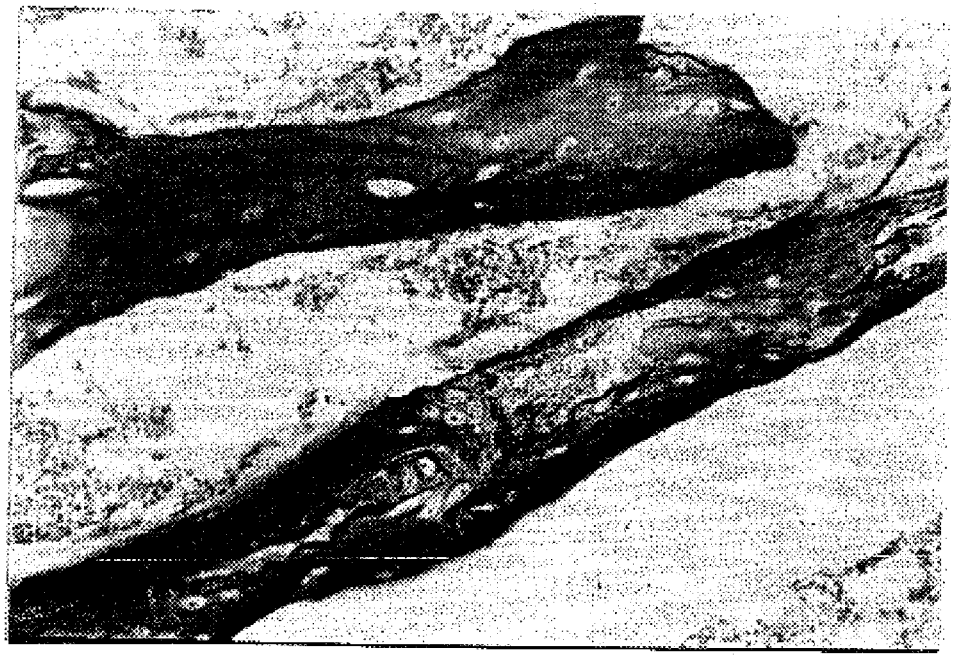
FIG. 19 is a diagram of silver staining in calcium L-threonate group, showing increased bone matrix and osteocytes and repaired microstructures.
Figure 20:
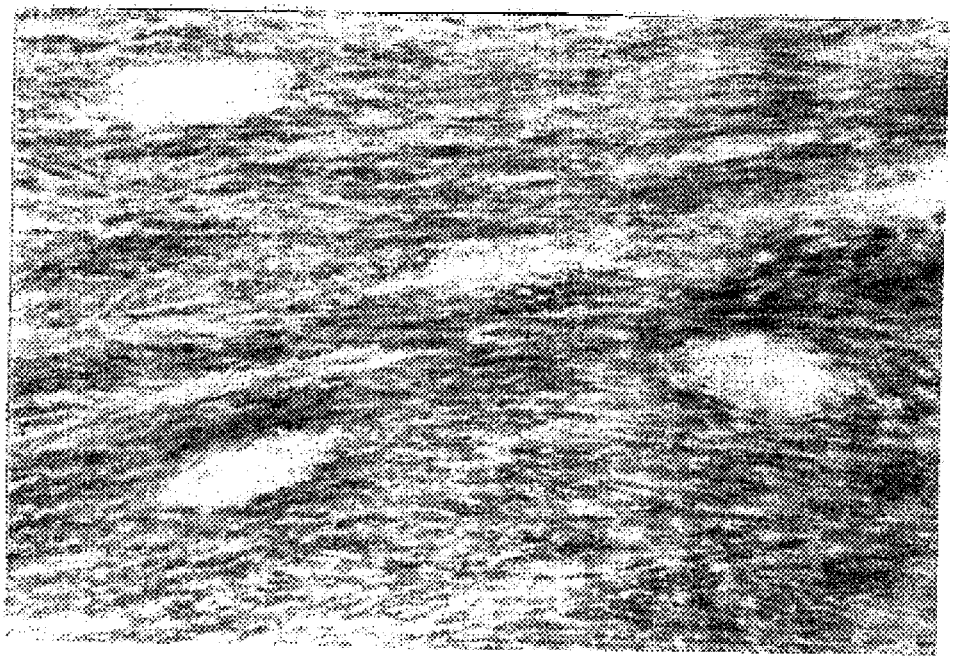
FIG. 20 is a diagram of silver staining in calcium L-threonate group, showing parallel, regular and abundant osteocollagenous fibers.

IV. The Results:

1. In the hybridization in situ of mRNA of collagen I, positive substances appeared brown yellow, and were found in the cytoplasm of osteocytes in the cortical bone (FIG. 18) and trabecular bone (FIG. 12). Positive substances were also found in the nucleus and cytoplasm of chondrocytes in the articular cartilage and epiphyseal plate. Some of the positive substances were found in cartilage capsule (FIGS. 2, 14, 17). The expression results of each group were shown in Table 1.

TABLE 1

Positive percentage of mRNA of collagen I by hybridization in situ of each group

| Groups | Case Nos. | Positive Case Nos. of osteocyte | Positive Case Nos. of chondrocyte |
|---|---|---|---|
| Blank-control group | 8 | 5 (62.5%) | 4 (50.0%) |
| Model-control group | 6 | 1 (16.7%) | 1 (16.7%) |

TABLE 1-continued

Positive percentage of mRNA of collagen I
by hybridization in situ of each group

| Groups | Case Nos. | Positive Case Nos. of osteocyte | Positive Case Nos. of chondrocyte |
|---|---|---|---|
| Caltrate-D group | 7 | 1 (14.3%) | 0 (0%) |
| Calcium citrate group | 6 | 2 (33.3%) | 0 (0%) |
| Sodium hydroxyethyl phosphate group | 6 | 2 (33.3%) | |
| Calcium L-threonate group I | 6 | 5 (83.3%)** | 5 (83.3%)** |
| Calcium L-threonate group II | 7 | 4 (57.1%)* | 4 (57.1%)* |
| Calcium L-threonate group III | 9 | 2 (22.2%) | 2 (22.2%) |

Note:
Compared with model-control group, *P < 0.05, **P < 0.01

The positive percentage was higher in Blank-control group, Calcium L-threonate groups I and II than other groups, wherein the positive percentage of Calcium L-threonate group I was significantly higher than Model-control group (P<0.05). Similar to the positive expression of mRNA of collagen I of osteocytes by hybridization in situ, the positive percentage of mRNA of collagen I of osteocytes by hybridization in situ in blank-control group, Calcium L-threonate groups I and II was relatively higher, wherein the expression percentage of calcium L-threonate group was significantly higher than that of model-control group (P<0.05).

Figure 5:
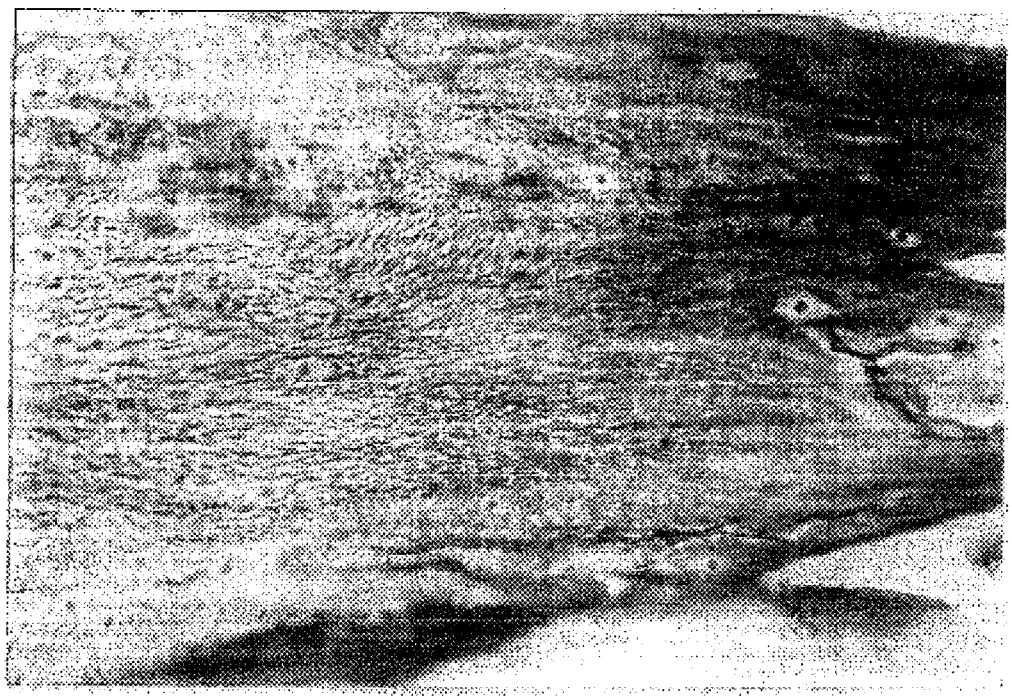
FIG. 5 is a diagram of silver staining in model group, showing sparse osteocollagenous fibers.
Figure 6:
FIG. 6 is a diagram of silver staining of metaphysis in model group, showing decreased synthesis of osteocollagenous fibers.
Figure 7:
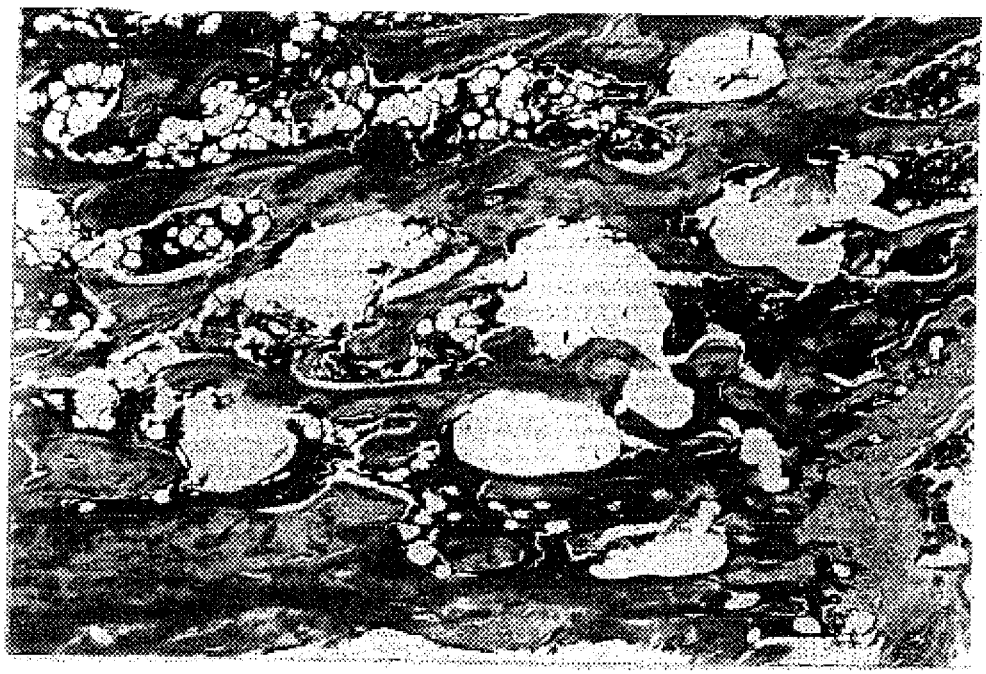
FIG. 7 is a diagram of MS staining of cancellous bone in caltrate-D group, showing sparse bone trabeculae and uneven distribution of osteocollagenous fibers.
Figure 11:
FIG. 11 is a diagram of silver staining in sodium hydroxyethyl phosphate group, showing disorganized dense oesteocollagenous fibers with unclear structure.

2. Positive substances of immunohistochemical staining of collagen I were mainly found in the chondrocytes in the articular cartilage and epiphyseal plate (FIGS. 2 and 7), especially significant in articular cartilage. Some were occasionally found in epiphyseal plate (FIGS. 5, 6 and 11) and distributed dispersedly. The expression results of each group were summarized in Table 2.

TABLE 2

Positive percentage of collagen I by
immunohistochemical staining of each group

| Group | Case Nos. | Positive Case Nos. of chondrocyte |
|---|---|---|
| Blank-control group | 8 | 6 (75.0%) |
| Model-control group | 6 | 2 (33.3%) |
| Caltrate-D group | 7 | 1 (14.3%)** |
| Calcium citrate group | 6 | 0 (0%)** |
| Sodium hydroxyethyl phosphate group | 6 | 2 (33.3%) |
| Calcium L-threonate group I | 6 | 4 (66.7%)□□ |
| Calcium L-threonate group II | 7 | 4 (57.1%)□□ |
| Calcium L-threonate group III | 9 | 3 (33.3%) |

Note:
Compared with model-control group, **P < 0.01
Compared with blank-control group, □□P < 0.01

The positive percentages of collagen I by immunohistochemistry in the blank-control group, calcium L-threonate group I and calcium L-threonate group II were relatively higher, however there were no statistically significant differences. The positive percentages of caltrate-D group and calcium citrate group were markedly lower than those of blank-control group (p<0.01).

3. Observation results of histochemical staining, wherein the blank-control group (see the attached FIGS. 1 and 2) was used as a "normal" reference standard:

(1) Model-control group in comparison with blank-control group: Articular cartilage shows retrograde affection. Both articular cartilage and epiphyseal plate became thin. Both the formation of bone collagen and synthesis of glycogen in the cartilage matrix were reduced. See the attached FIGS. 3, 4, 5 and 6. The reduction of newly formed bone and microfracture of bone corresponded to the pathological changes of osteoporosis.

Figure 8:
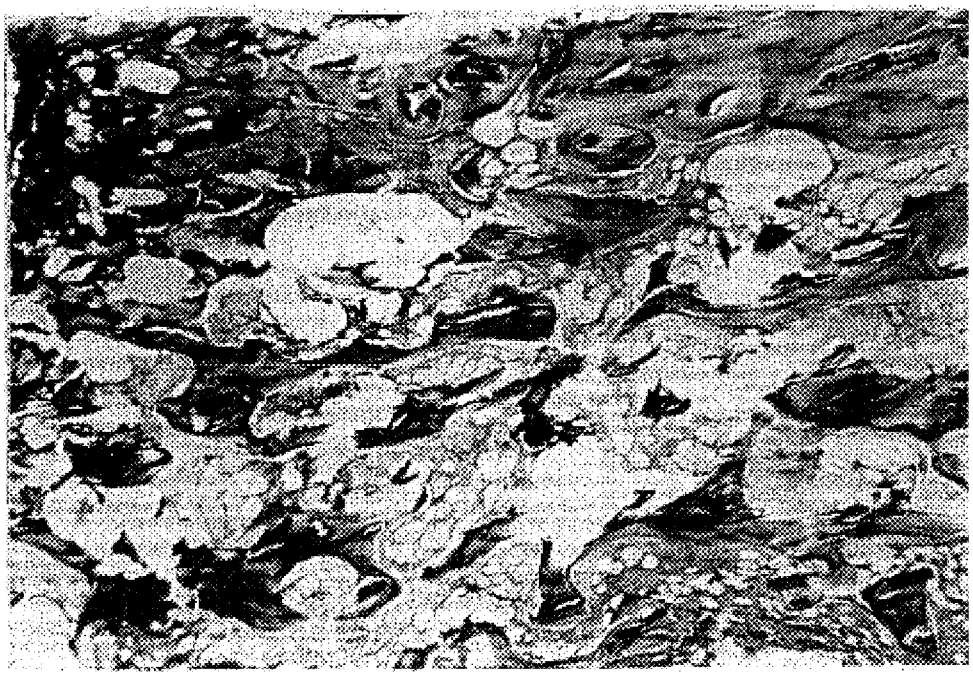
FIG. 8 is a diagram of histochemical staining of glycogen of cancellous bone in caltrate-D group, showing sparse bone trabeculae and positive glycogen (+).
Figure 9:
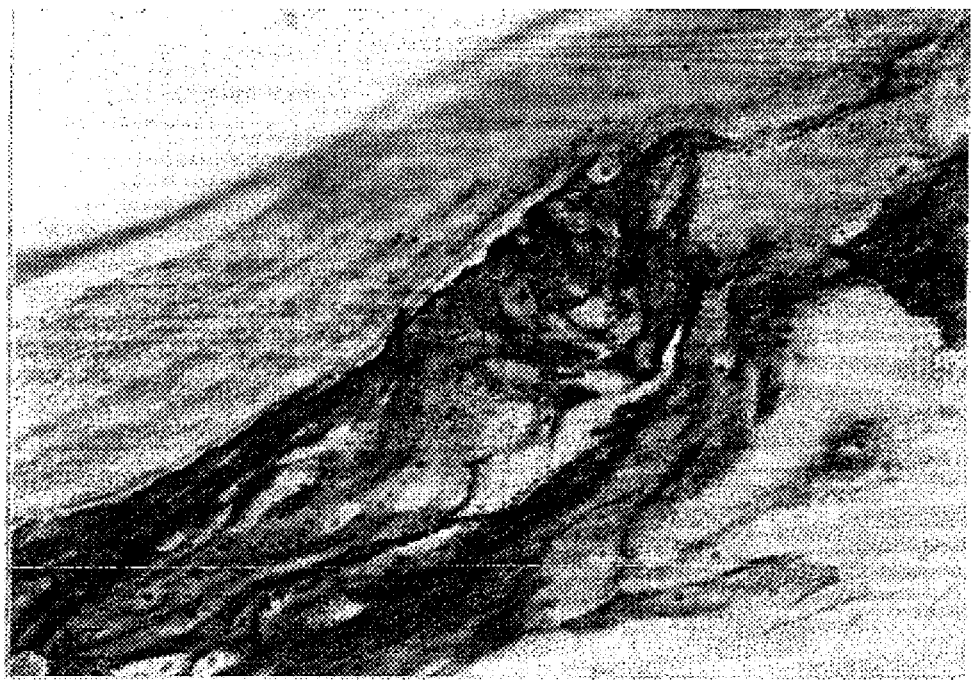
FIG. 9 is a diagram of histochemical silver staining of cortical bone in caltrate-D group, showing short, thin and scattered osteocollagenous fibers.

(2) Caltrate-D group: The calcification of cell in articular cartilage and epiphyseal cartilage was similar to that of blank-control group, however, the cartilage matrix showed slight retrograde affection, and the formation of bone collagen and synthesis of glycogen decreased. See FIGS. 7 and 8. Silver stained fibers were less and appeared as dot (FIG. 9). The formation of bone was less than that of the blank-control group.

Figure 10:
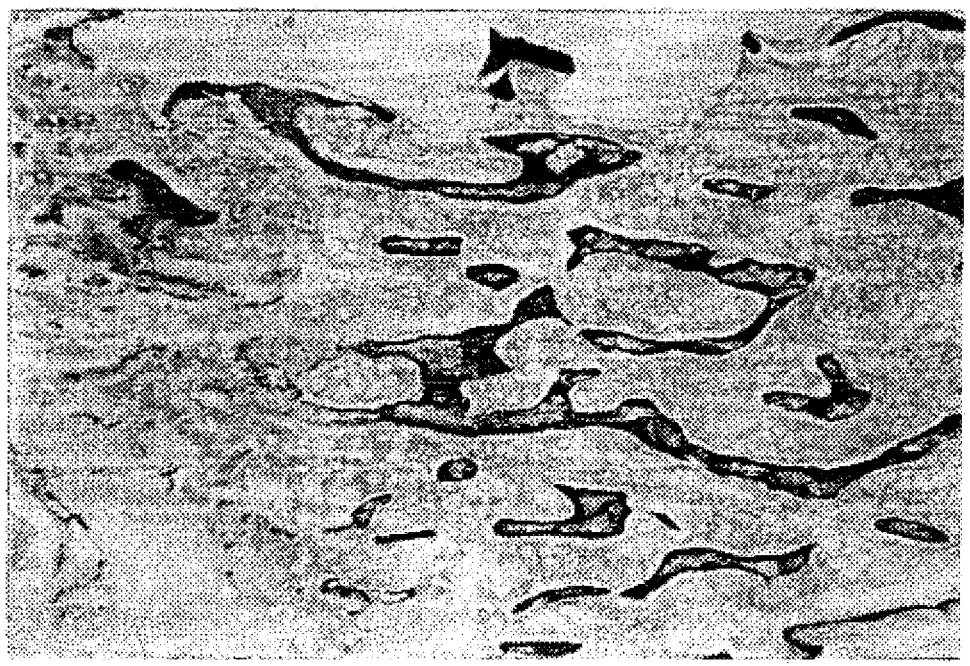
FIG. 10 is a diagram of silver staining in sodium hydroxyethyl phosphate group, showing sparse oesteocollagenous fibers.
Figure 13:
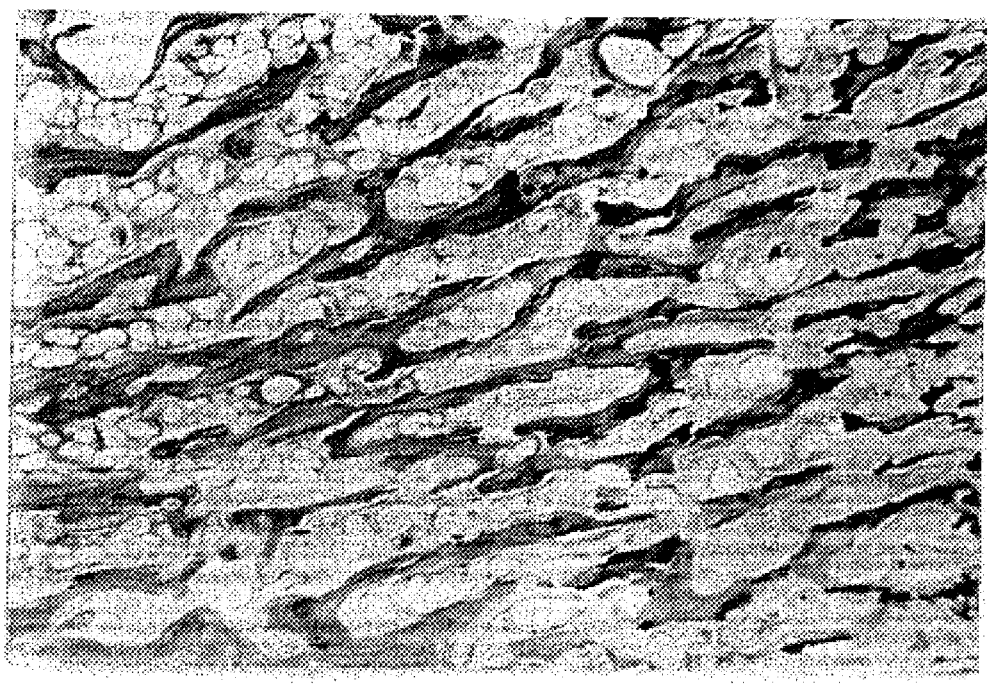
FIG. 13 is a diagram of histochemical staining of glycogen in hydroxylethyl sodium phosphate group, showing excessive and disorganized bone trabeculae in cancellous bone and less glycogen.

(3) Sodium hydroxyethyl phosphate group: Articular cartilage developed retrograde affection. Epiphyseal chondrocytes highly proliferated, their architecture was disorganized and appeared as osteoid. They did not undergo the process of ossification and the bone was not mature. The silver stained substances were dense and disorganized. See FIGS. 10 and 11. The endosteum thickened, and the formation of bone collagen and synthesis of glycogen decreased. See FIGS. 12 and 13.

Figure 15:
FIG. 15 is a diagram of histochemical MS staining of epiphyseal cartilage in calcium L-threonate group, showing increased chondrocytes, abundant blood vessels and increased collagen fibers.
Figure 16:
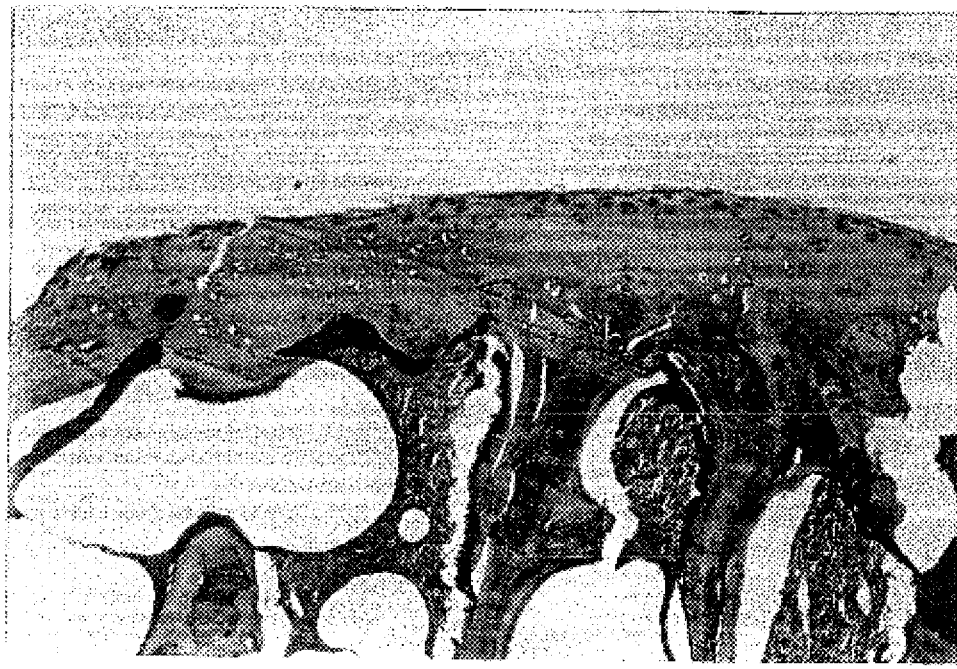
FIG. 16 is a diagram of histochemical MS staining of articular cartilage in calcium L-threonate group, showing incrassated cartilage matrix and increased chondrocytes.

(4) Calcium L-threonate group: The amount, volume and texture microstructure of the chondrocytes in articular cartilage and epiphyseal plate showed different degree of improvement (in comparison with the blank-control group). Cartilage collagen fibers and matrix thickened (see FIGS. 15 and 16). The amount of osteocytes increased and the volume enlarged. The formation of collagen increased. The content of glycogen was obviously higher than that in the blank-control group. The formation of new bone was increased (see FIGS. 14, 17, 18, 19 and 20). Meanwhile, bone canaliculi proliferated and nourishing blood vessels of the bone increased.

(5) Calcium citrate group: The formation of matrix and collagen in the articular cartilage and epiphyseal cartilage and the synthesis of glycogen increased. However, the progress of calcification and ossification was slow. The newly formed bones were less than those of the blank-control group.

IV. Conclusions

The experiment results showed that:

1. The hybridization in situ of mRNA of collagen I showed that calcium L-threonate significantly increased the positive expression percentage of mRNA of collagen I in osteocyte. Accordingly, the formation of bone collagen was increased and the bone formation was promoted.

2. The results of hybridization in situ of mRNA of collagen I and immunohistochemical test of collagen I demonstrated that in calcium L-threonate group I, the positive expression percentage of chondrocyte in articular cartilage and epiphyseal cartilage was significantly increased. Similar results were also shown in the calcium L-threonate group II and III.

The increased expression of articular chondrocytes could facilitate the formation of articular cartilage matrix. The increased expression of chondrocyte in the epiphyseal plate could facilitate the formation of cartilage matrix in the epiphyseal plate, and accordingly facilitating the formation of primary trabeculae and increasing the bone mass.

3. Histochemistry of T-B glycogen, M-S collagen and V-K silver staining demonstrated that calcium L-threonate had the effects of facilitating the formation of bone collagen and synthesis of proteoglycan, and protected the normal structure of articular cartilage, retarded the retrograde affection of articular cartilage, was helpful to the growth and development of epiphyseal cartilage and improved the process of autoskeleton in epiphyseal cartilage. The physical arrangement of the newly formed bone corresponded with biomechanical structure.

4. The bone collagen forming protein had avidity with calcium, causing calcium L-threonate to act as a carrier, which carried calcium to the designated object and combined with bone collagen to form bone.

5. Calcium L-threonate facilitated the formation of nourishing blood vessels and improved the microcirculation of bone.

It could be seen from the above-mentioned conclusions that calcium L-threonate had the effects of preventing and treating senile retrograde affections of bone and articular cartilage, facilitating the healing of cartilage damage and repairing of cartilage tissue, and improving the microcirculation system, and retarding the senile progress of skeleton.

That which is claimed:

1. A method for treating cartilage related diseases, comprising administering an effective amount of calcium L-threonate to a subject suffering from a cartilage related disease, wherein said cartilage related disease is one or more selected from the group consisting of osteoarthritis, rheumatoid arthritis, multiple chondritis, articular cartilage damage, and osteochondrosis.

2. The method according to claim 1, wherein said cartilage related disease is rheumatoid arthritis.

3. The method according to claim 1, wherein said cartilage related disease is osteoarthritis.

4. The method according to claim 1, wherein said cartilage related disease is multiple chondritis.

5. The method according to claim 1, wherein said cartilage related disease is articular cartilage damage.

6. The method according to claim 1, wherein said cartilage related disease is osteochondrosis.

7. The method according to claim 1, wherein calcium L-threonate is administered in an amount in the range of 0.5–12 gram/day.

8. The method according to claim 7, wherein calcium L-threonate is administered in an amount in the range of 3–7 gram/day.

9. The method according to claim 1, wherein calcium L-threonate is administered orally.

* * * * *